United States Patent [19]

Wright et al.

[11] 4,108,872

[45] Aug. 22, 1978

[54] 7-DIMETHYLAMINO-4-CHROMANONE

[75] Inventors: George C. Wright; Marvin M. Goldenberg, both of Norwich, N.Y.

[73] Assignee: Morton-Norwich Products, Inc., Norwich, N.Y.

[21] Appl. No.: 812,125

[22] Filed: Jul. 1, 1977

[51] Int. Cl.$^2$ .......................................... C07D 311/22
[52] U.S. Cl. ................................. 260/345.2; 424/283
[58] Field of Search ..................................... 260/345.2

[56] References Cited

U.S. PATENT DOCUMENTS 4,062,870  12/1977   Watts ................................. 260/345.2

*Primary Examiner*—Nicky Chan
*Attorney, Agent, or Firm*—Anthony J. Franze

[57] ABSTRACT

The compound 7-dimethylamino-4-chromanone is useful as an anti-inflammatory agent.

1 Claim, No Drawings

7-DIMETHYLAMINO-4-CHROMANONE

This invention is concerned with the chemical compound 7-dimethylamino-4-chromanone. It has been found that it possessed pharmacological activity. More particularly, it has been found to exhibit anti-inflammatory activity upon peroral administration. For example, when administered to rats at a dose of about 300 mg/kg suspended in aqueous methylcellulose, edema induced by the administration of carrageenin to rats is suppressed [Winter et al. P.S.E.B.M. 111:544 (1962)].

This compound can be readily formulated into pharmaceutical compositions such as elixirs, tablets, capsules, suspensions and the like using commonly employed carriers and excipients with which there is no incompatibility.

In order that this invention may be readily available to and understood by those skilled in the art, the following directions represent the currently preferred method for making it.

A. 3-(m-Dimethylaminophenoxy)propionitrile

A 407 g (7.68 moles) portion of acrylonitrile and 500 g (3.65 moles) of m-dimethylaminophenol were placed in a 3-l, 3-necked flask equipped with a stirrer and reflux condenser with a drying tube. The solution was treated with 4 g (0.17 mole) of metallic sodium, over 0.7 hr., with an observed temperature rise from 10° to 24°. The reaction mixture was heated to reflux over 0.8 hr., refluxed for 22 hrs., cooled, treated with 11 ml of glacial acetic acid and the excess acrylonitrile removed under reduced pressure. The residue was taken up in 3.8-l of ether, decanted from a purple resinous material, stored over Darco overnight and filtered. The filtrate was stripped of ether under reduced pressure to give 590 g (80%) of the desired nitrile (brown).

B. 3-(m-Dimethylaminophenoxy)propionic acid

A 590 g (3.11 moles) portion of 3-(m-dimethylaminophenoxy)-propionitrile was added, over a 0.2 hr. period, to 4-l of concentrated hydrochloric acid, contained in a 5-l, 3-necked flask equipped with a stirrer and reflux condenser. The reaction mixture was heated to 85% (via. a mantle) over 1 hr., refluxed for 4 hrs. with gradual rise to 109°, stored overnight at room temperature and stripped hard under reduced pressure. The purple crystalline residue was taken up in 750 ml of isopropanol. The purple crystalline solid was washed with 400 ml of isopropanol, taken up to 750 ml of isopropanol, warmed on a steam bath for 2 hrs. and filtered. The pink crystalline solid was washed with 300 ml of isopropanol, ether and dried; m.p. 170°-183° dec. Yield: 460 g.

The hydrochloride, 460 g, was taken up in 2.7-l of $H_2O$ adjusted to pH 6-7 with 161 g (1.91 mole) of $NaHCO_3$, using rapid stirring. The reaction mixture was stored in 1 hr. at room temperture and filtered. The cream colored crystalline solid was washed with 1-l of $H_2O$ and air dried to a contant weight; m.p. 108-109° Yield: 160 g (25%).

The filtrate (no washings) was concentrated to 1/5 volume, stored at room temperture overnight and filtered. The white crystalline solid was washed with 300 ml of $H_2O$, and air dried to constant weight; m.p. 108-120° gel. Yield: 100 g (15%).

The crude products were combined, 336 g, and recrystallized for 6 hrs., and filtered. The gray needles were washed with 100 ml of isopropanol, ether, and dried; m.p. 107°-108° corr. Yield: 82 g (13%).

Anal. Calcd. for $C_{11}H_{15}NO_3$: C, 63.14; H, 7.23; N, 6.7. Found C, 63.42; H, 7.34; N, 6.71.

C. 7-Dimethylamino-4-chromanone

To 650 g of polyphosphoric acid (at 56°) was added 130 g (0.62 mole) of B. over 10 min., using rapid mechanical stirring and a water bath to maintain the temperature below 80°. The reaction mixture was maintained at 70°-80° for 4.3 hrs., stored overnight at room temperature, rewarmed to 50° and poured (with rapid stirring) into 2.8-l of cold $H_2O$ (11°). The hydrolysis solution was adjusted to pH 7 with 900 g (10.7 moles) of $NaHCO_3$ stored 1 hr. at room temperature and filtered. The green crystalline solid was washed with 700 ml of $H_2O$, and air dried to a constant weight; m.p. 109°-120°. Yield: 94 g (80%).

The product was recrystallized from 375 ml of ethanol refrigerated, and filtered. The yellow-green solid was washed with 100 ml of ethanol and dried; m.p. 154°-156° corr. Yield: 44 g (37%).

Anal. Calcd. for $C_{11}H_{13}NO_2$ : C, 69.09; H, 6.85; N, 7.33. Found: C, 69.05; H, 6.70; N, 7.41.

What is claimed is:

1. The compound 7-dimethylamino-4-chromanone.